United States Patent
Sakai et al.

(10) Patent No.: US 8,963,089 B2
(45) Date of Patent: Feb. 24, 2015

(54) DRUG DETECTION DEVICE AND DRUG DETECTION METHOD

(75) Inventors: Shiho Sakai, Osaka (JP); Tomohiro Fukuma, Osaka (JP)

(73) Assignee: Otsuka Pharmaceutical Co., Ltd., Tokyo (JP)

(*) Notice: Subject to any disclaimer, the term of this patent is extended or adjusted under 35 U.S.C. 154(b) by 0 days.

(21) Appl. No.: 14/129,625

(22) PCT Filed: Jun. 27, 2012

(86) PCT No.: PCT/JP2012/066445
§ 371 (c)(1),
(2), (4) Date: Dec. 27, 2013

(87) PCT Pub. No.: WO2013/002290
PCT Pub. Date: Jan. 3, 2013

(65) Prior Publication Data
US 2014/0117239 A1 May 1, 2014

(30) Foreign Application Priority Data

Jun. 28, 2011 (JP) .................................. 2011-143253

(51) Int. Cl.
*G01J 3/42* (2006.01)
*G01J 3/06* (2006.01)
*G01N 21/359* (2014.01)

(52) U.S. Cl.
CPC .... *G01J 3/42* (2013.01); *G01J 3/06* (2013.01); *G01N 21/359* (2013.01)

USPC .................................................... 250/339.07

(58) Field of Classification Search
CPC .......... G01J 3/06; G01J 3/42; G01N 21/3563; G01N 21/359; G01N 21/85; G01N 21/9508
USPC ............................ 250/338.1, 339.06, 339.07
See application file for complete search history.

(56) References Cited

FOREIGN PATENT DOCUMENTS

| JP | 07-245284 A | 9/1995 |
|---|---|---|
| JP | 07-260770 A | 10/1995 |
| JP | 2003-104333 A | 4/2003 |
| JP | 2008-143653 A | 6/2008 |
| JP | 2009-020004 A | 1/2009 |
| JP | 2010-175528 A | 8/2010 |

*Primary Examiner* — Mark R Gaworecki
(74) *Attorney, Agent, or Firm* — Sughrue Mion, PLLC (57) ABSTRACT

A device for detecting a drug remaining in a target area that includes an irradiation unit configured to irradiate the area with a light beam including near-infrared light, a spectroscope on which reflected light from the area is incident, and a near-infrared imaging unit configured to capture a spectrum obtained through dispersion of the reflected light by the spectroscope, to generate image data, and to capture each spectrum of a predetermined number of pixels within the area. A control unit is configured to process the image data, to compute average spectral data of the area by averaging the spectrums of the pixels, and to compute an amount of the drug corresponding to the average spectral data, based on an equation. A storage unit is configured to store an equation expressing a relationship between a prescribed amount of a drug and spectral data based on the spectrum.

8 Claims, 7 Drawing Sheets

■ Main Ingredient + Diluent

Mixtures containing 0, 50 100 μg/100cm² samples of main ingredient mixed with diluent each dripped in 10 and 20 μg amounts ■ Main Ingredient 0, 10, 20, 30 40, 50, 60, 70, 80, 90, 100 μg/100cm² samples

DRUG DETECTION DEVICE AND DRUG DETECTION METHOD

CROSS REFERENCE TO RELATED APPLICATION

This application is a National Stage of International Application No. PCT/JP2012/066445, filed on Jun. 27, 2012, claiming priority based on Japanese Patent Application No. 2011-143253, filed Jun. 28, 2011, the contents of all of which are incorporated herein by reference in their entirety.

TECHNICAL FIELD

The present invention relates to a drug detection device and a drug detection method for detecting a drug remaining in a target area.

BACKGROUND ART

Conventionally, drug manufacture can involve a plurality of drugs being manufactured on one production line. In this case, when the manufacture of one drug ends, the production line is cleaned, and a different drug is manufactured. Cleaning of a production line is described in Patent Literature 1, for example. However, in order to check that none of the drug that was previously manufactured remains after the production line has been cleaned, the residual amount of the drug is computed by wiping a predetermined location of the line with a test substance and analyzing the test substance.

CITATION LIST

Patent Literature

[PTL 1] JP 2003-104333A

SUMMARY OF INVENTION

However, there is a problem with the above method in that time is required to analyze the residual amount of a drug, and the production line has to be stopped while the residual amount is being computed. Thus, there is a problem in that production efficiency drops.

The present invention was made in order to resolve the above problems, and an object of the invention is to provide a drug detection device and a drug detection method that are able to compute the residual amount of a drug quickly and in a contactless manner.

TECHNICAL PROBLEM

A drug detection device according to the present invention is for detecting a drug remaining in a target area, and includes an irradiation unit configured to irradiate a target area with a light beam that includes near-infrared light, a spectroscope on which reflected light from the target area is incident, a near-infrared imaging unit configured to capture a spectrum obtained through dispersion of the reflected light by the spectroscope and to generate image data, a control unit configured to process the image data, and a storage unit configured to store an equation expressing a relationship between a prescribed amount of a drug and spectral data that is based on the spectrum. The near-infrared imaging unit is configured to capture each spectrum of a predetermined number of pixels allocated within the target area, and the control unit is configured to compute average spectral data of the area by averaging the spectrums of the pixels, and to compute an amount of the drug corresponding to the average spectral data, based on the equation stored in the storage unit.

According to this configuration, the residual amount of a drug can be computed by analyzing a spectrum obtained through dispersion of reflected light from a target area. Accordingly, since the residual amount of a drug can be checked in a short time, it is possible, for example, in the case of checking the residual amount of a drug on a production line, to perform the detection operation in a short time, thus enabling the time for which the production line is stopped to be minimized, and manufacturing efficiency to be improved. Also, with the above device, even though the spectrum of each pixel allocated to the entire target area is acquired, average spectral data obtained by averaging the spectrums of the pixels is used to compute the amount of a drug. Thus, the volume of data can be reduced, and the amount of a drug can be computed quickly. Also, the device is suited to data transmission by wireless or the like, enabling device versatility to also be improved.

In the above drug detection device, a configuration can be adopted in which a probe incorporating a light receiving unit for receiving reflected light is further provided, and reflected light is incident on the spectroscope via the light receiving unit. Handling is facilitated when such a probe is used. At this time, the irradiation unit can also be provided outside of the probe or incorporated in the probe.

In the case of incorporating the irradiation unit, at least an irradiation surface from which the irradiation unit emits a light beam can be incorporated in the probe, for example. At this time, disposing the light source at a distance from the probe and supplying the amount of light from the light source through a known cable such as a fiber cable facilitates measurement since the area around the measurement point is kept orderly and excessive increases in temperature can also be prevented.

Although the irradiation surface can have various configurations, a configuration can be adopted in which the irradiation surface surrounds a light receiving surface on which the light receiving unit receives reflected light, for example, so as to be able to irradiate the light beam uniformly onto a target area.

In addition, in the above drug detection device, the near-infrared image imaging unit can be a line sensor camera, and a mirror scanner that scans the target area can be further provided. Scanning the target area in one direction with the mirror scanner enables the light reflected from the target area to be incident on the spectroscope via the mirror scanner.

According to this configuration, even when using a line sensor camera which generally requires the target to be moving, a stationary object can be imaged by using a mirror scanner. Also, for example, the camera and the spectroscope can be disposed at a distance from the target area using a cable such as an optical fiber cable, and the area around the measurement point can be made compact. Accordingly, machine operability is facilitated even when a drug detection device having this configuration is used in a production line.

In the above drug detection device, a supporting member that supports the mirror scanner and opposes the target area can be further provided. At this time, the opposing surface where this supporting member opposes the target area preferably is black in color. This is for the following reasons. That is, there is a possibility of a portion of a light beam including near-infrared light irradiated from the irradiation unit being reflected by the opposing surface of the supporting member after being reflected by the target area, and an image of the opposing surface being projected onto the target area and scanned by the mirror scanner. In view of this, when the opposing surface is black in color, as described above, reflection of the light beam can be prevented, and projection onto the target area can be reduced as a result. A drop in the accuracy of drug detection can thereby be prevented.

A drug detection method according to the present invention is a drug detection method for detecting a drug remaining in a target area, and includes a step of irradiating a target area with a light beam that includes near-infrared light, a step of causing reflected light from the target area to be incident on a spectroscope, a step of capturing, with a near-infrared imaging device, a spectrum obtained through dispersion of the reflected light by the spectroscope, and generating image data, a step of processing the image data, and a step of storing an equation expressing a relationship between a prescribed amount of a drug and spectral data that is based on the spectrum. The near-infrared imaging device is configured to capture each spectrum of a predetermined number of pixels allocated within the target area, and in the step of processing the image data, average spectral data of the area is computed by averaging the spectrums included in the image data, and an amount of the drug corresponding to the average spectral data is computed based on the equation.

EFFECT OF INVENTION

As described above, according to the present invention, since the residual amount of a drug can be computed in a short time, it is possible, for example, in the case of checking the residual amount of a drug on a production line, to perform operations in a short time, enabling the duration for which the production line is stopped to be minimized and manufacturing efficiency to be improved.

REFERENCE SIGN LIST

11 Supporting member
12 Mirror scanner
13 Light source (irradiation unit)
114 Opposing surface
3 Spectroscope
4 Line sensor camera (near-infrared imaging unit, near-infrared imaging device)
5 Computer (control unit, storage unit)
7 Probe
711 Light receiving surface
712 Irradiation surface
714 Trigger button

[DESCRIPTION OF EMBODIMENTS]

First Embodiment

Figure 1:
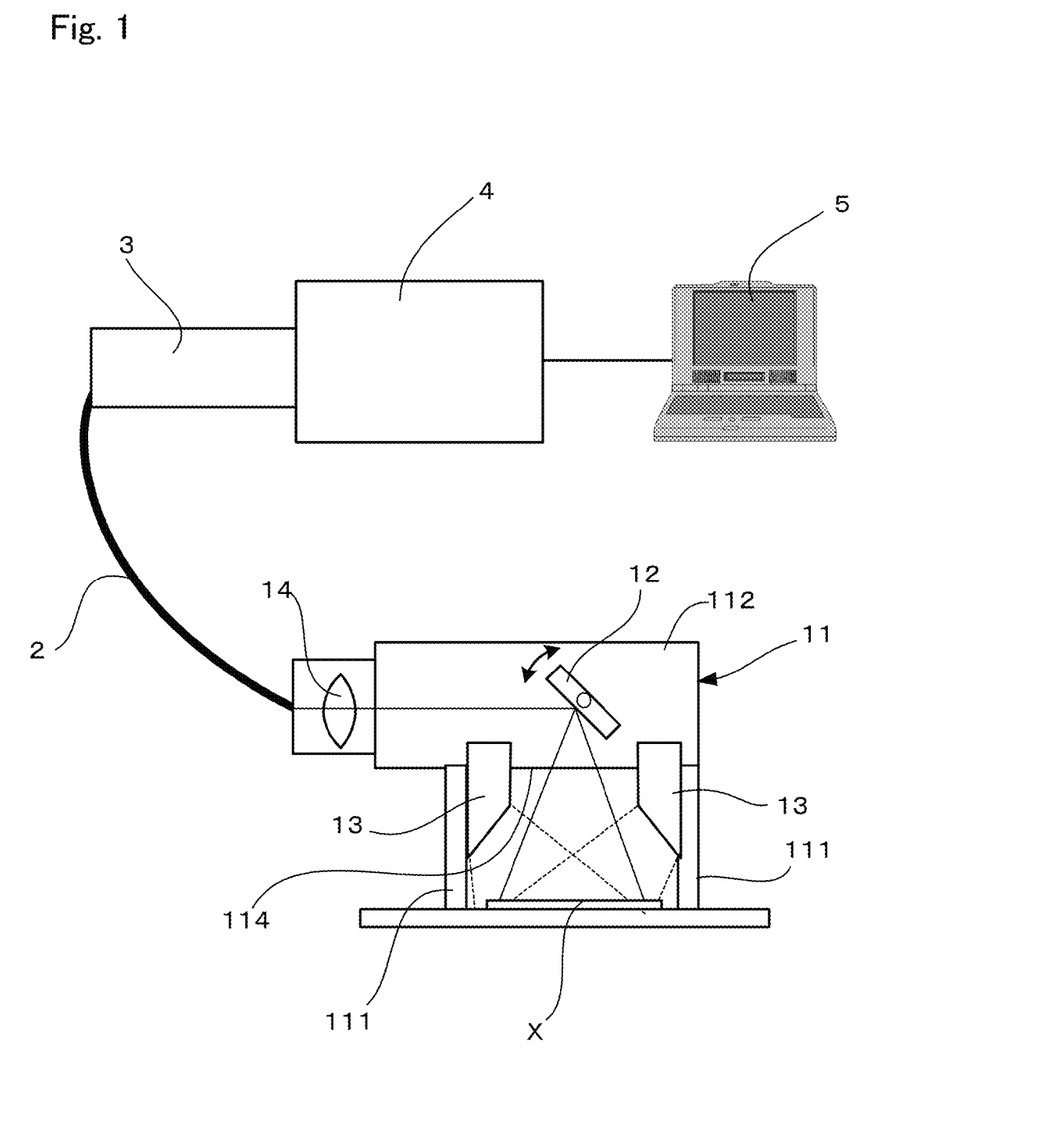
FIG. 1 is a schematic configuration diagram showing a first embodiment of a drug detection device according to the present invention.

Hereinafter, a first embodiment of a drug detection device according to the present invention will be described with reference to the drawings. FIG. 1 is a schematic configuration diagram of the drug detection device according to the present embodiment.

The drug detection device according to the present embodiment is for detecting the amount of a drug remaining in a target area. This drug detection device can, for example, be used in order to check for residual amounts of a drug, after cleaning the production line of the drug. As shown in FIG. 1, this device is provided with a supporting member 11 that covers a target area X from above, a spectroscope 3 that is connected to this supporting member 11 via optical fiber 2, and a line sensor camera 4 capable of capturing near-infrared light. In addition, a computer 5 that performs driving of the device, data processing, and the like is attached. The supporting member 11 is provided with a box-shaped ceiling portion 112 that is supported by a plurality of legs 111 that are disposed around the target area X and covers the target area X from above. A swingably supported mirror scanner 12 is attached to the ceiling portion 112 and scans the target area X in one direction. The mirror scanner 12 can be driven by the computer 5. An opposing surface 114 where the ceiling portion 112 opposes the target area X is black in color and prevents light from being reflected. Also, a pair of light sources (e.g., halogen lamps, etc.) 13 that irradiate the target area X with light beams (white light, etc.) that include near-infrared light are attached to the ceiling portion 112 so as to evenly illuminate the target area X. Furthermore, a lens 14 for focusing light reflected by the mirror scanner 12 and sending the reflected light to the optical fiber 2 is attached to one end of the ceiling portion 112. Here, the end of the optical fiber 2 is disposed opposing the lens 14 as a light receiving surface. Thus, since the supporting member 11 has a compact structure that does not include a spectroscope, camera or the like, the supporting member 11 can be carried around by itself, and residual amounts of a drug can be measured at desired positions.

The line sensor camera 4 is attached to the optical fiber 2 via the spectroscope 3. Known devices can be used for the spectroscope 3 and the line sensor camera 4. For example, a line sensor camera having sufficient sensitivity to near-infrared light with a wavelength of around 900 to 2500 nm can be used for the line sensor camera 4. Also, the line sensor camera 4 is connected to the computer 5, and processes image data.

While the device is for computing the amount of a drug remaining in the target area X, an equation expressing the relationship between a prescribed amount of the drug and spectral data that is based on the spectrum of reflected light from the target area needs to be created prior to computing the residual amount of the drug. Hereinafter, creation of the equation will be described.

Figure 2:
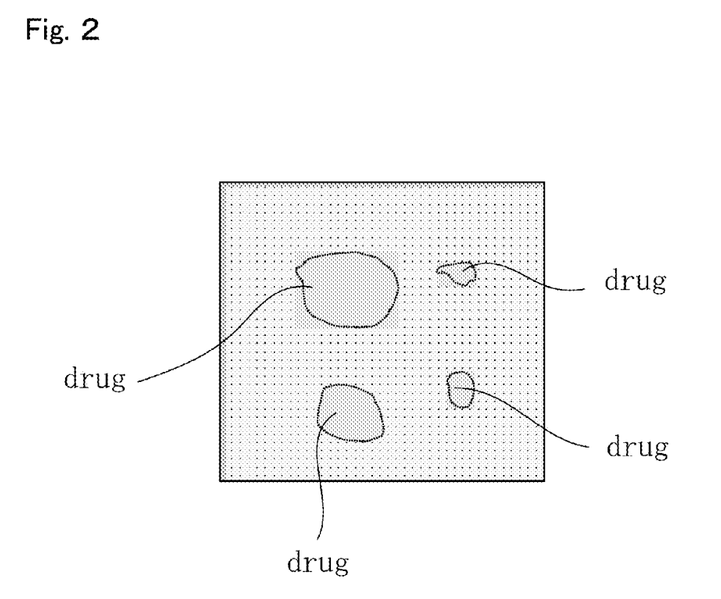
FIG. 2 is a plan view showing an exemplary sample board.

To begin with, an example of a sample creation method for creating the equation will be shown. First, a SUS board of the same material as the production line is prepared, an aqueous or organic solvent obtained by dissolving or dispersing the drug is dripped onto one surface of the SUS board, and the solvent is then removed by distillation. Square SUS board having 10 cm sides can be used for the sample board, for example. Next, a plurality of sample boards whose amounts of the drug have been suitably changed are created. For example, around ten samples of 0 to 200 μg/100 cm$^2$ of the drug are created. Also, the samples preferably are prepared by mixing a diluent with the drug. Note that the drug may be dripped onto one place on the sample board, or may be randomly dripped onto a plurality of places on the sample board, as shown in FIG. 2. Also, the material used for the sample board is the same material as areas to which the drug will adhere in the drug manufacturing device. Accordingly, sample boards need to be created for each of the materials of the adhesion areas.

Figure 3:
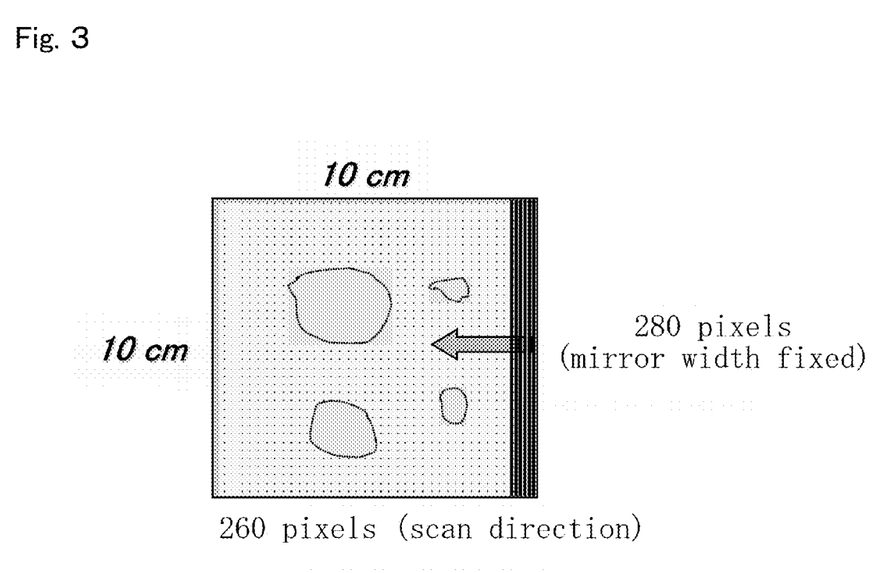
FIG. 3 illustrates scanning of a sample board by a mirror scanner.

Next, the near-infrared spectrum is measured using the sample boards created as described above. First, a sample board is disposed under the supporting member 11 of the device. The light sources 13 irradiate the sample board with light beams that include near-infrared light, and the sample board is scanned by the mirror scanner 12. As described above, this device uses a line sensor camera 4, and imaging being performed with a predetermined number of pixels allocated to the target area X. For example, from the perspective of measuring 10 cm sides, measurement is performed with 300 pixels allocated to the line that is to undergo scanning, and with 300 pixels allocated in the scanning direction. The number of pixels in the scanning direction is, however, determined by the relationship between the drive speed of the mirror scanner 12 and the shutter speed of the camera 4. In this example, the spectrums of 90000 pixels can thus be obtained from one sample board. Note that the number of pixels allocated to the target area X can be set from 51200 to 409600 pixels, for example. Specifically, as shown in FIG. 3, pixel lines are imaged one at a time from one end of the sample board to the other end while swinging the mirror scanner 12, resulting in 300 lines being imaged in total. The mirror scanner 12 reflects reflected light from the sample board, and this reflected light is focused by the lens 14 of the ceiling portion 112 of the supporting member 11, and thereafter sent to the spectroscope 3 through the optical fiber 2. Note that in scanning a sample board with the mirror scanner 12, preferably data from one direction is not only measured a plurality of times (e.g., 10 times) but data is collected by scanning the mirror scanner from the directions of all four sides (e.g., 10 times×4 directions) to take into account error.

Figure 4:
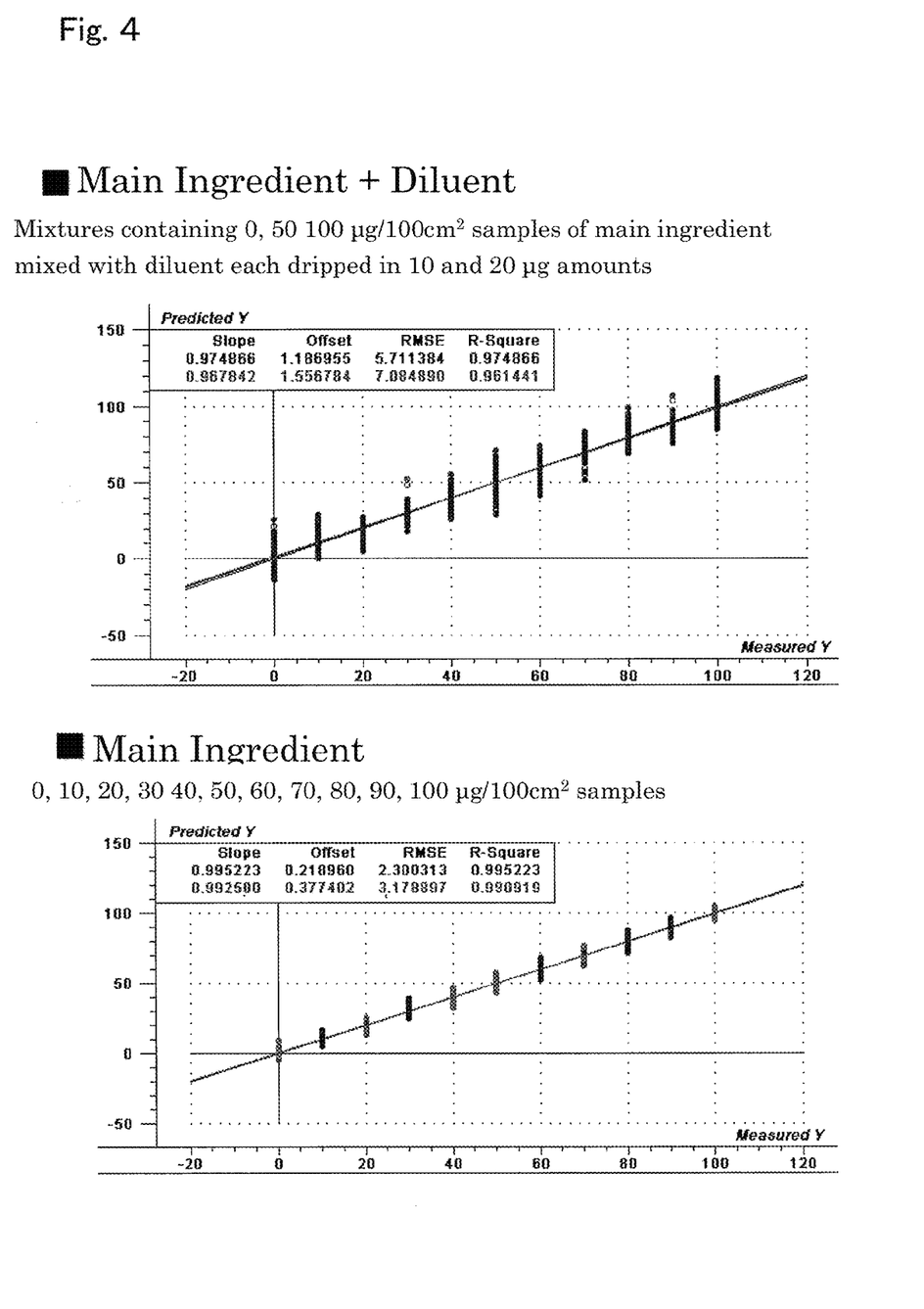
FIG. 4 shows an exemplary calibration curve.

An optical spectrum is formed when reflected light is incident on the spectroscope 3. An image of this optical spectrum is formed on the imaging surface of the line sensor camera 4 and image data is generated, and the generated image data is then sent to the computer 5. The computer 5 performs processing such as the following. First, the spectrums of 90,000 pixels, as one example, are obtained for each sample board in one measurement, and then these spectrums are averaged and one piece of average spectral data is computed per sample board in one measurement. The processing is repeated ten times per direction, and is also similarly performed for the other three directions. Averaging can be performed by computing the arithmetic mean, for example. The arithmetic mean is computed by adding together the spectrums of all the pixels obtained from the target area, and dividing the resultant value by the number of pixels. Next, calibration curves, such as shown in FIG. 4, for example, are created by using a known method such as multivariate analysis, for example, to analyze the plurality of pieces of average spectral data obtained from the sample boards, and calculating the correlation with the amounts of the drug dripped on the sample boards. In FIG. 4, the horizontal axis shows the amount of the drug dripped on each sample board, and the vertical axis shows the predicted amount of the drug obtained from the result of multivariate analysis (all in units of µg/100 m$^2$; rebamipide is given as the main ingredient in the drug). At this time, calibration curves having a correlation coefficient of at least 0.98 are preferably created. Note that multivariate analysis can be performed using PLS regression analysis, for example. The number of the principal components (number of PCs) used at this time can be from 5 to 20, for example, with an optimal number of PCs preferably being set since over-fitting occurs and reproducibility deteriorates when there are too many PCs. A known cross-validation method is utilized in verifying the calibration curves.

Thus, deriving an equation based on created calibration curves enables the amount of a drug remaining on the production line to be computed based on the average spectrum computed from the sample measurements. Data for the equation is saved in a storage unit incorporated in the computer 5, such as an SSD or a hard disk of the computer, for example. Preferably data for such an equation is created for each drug and saved on the hard disk, and then read out as appropriate when measuring the residual amount of a drug. The data can also be saved on a storage medium such as a CD-ROM or a flash memory, and read out as appropriate. Furthermore, these data can also be saved on an external storage medium, and then read out for use on the computer 5 via a network. Accordingly, the storage unit of the present invention also includes a volatile memory that temporarily saves data read out from an external storage medium, in addition to a nonvolatile memory or a hard disk within the computer.

Next, a method for measuring the residual amount of a drug using the abovementioned drug detection device will be described. First, the supporting member 11 is disposed so as to cover the target area X. For example, the supporting member 11 is disposed in a position where the residual amount of a drug is to be checked, such as within the production line of the drug. Next, the light sources 13 irradiate the target area X with light beams that include near-infrared light, and the mirror scanner 12 is driven and scans the reflected light of the target area X. At this time, since the opposing surface 114 opposing the target area X is black in color, projection of an image of the opposing surface 114 onto the target area X can be reduced. The reflected light thus obtained is sent to the line sensor camera 4 via the lens 14, the optical fiber 2 and the spectroscope 3, and image data is then sent to the computer 5. The optical spectrums of a predetermined number of pixels are thus obtained. In the computer 5, the average spectrum is computed from the obtained optical spectrums, and the amount of the drug is computed by using the equation, as described above. If the computed residual amount of the drug in a predetermined location is less than or equal to a determination reference value, the production line is operated, and if the computed residual amount is higher than the determination reference value, cleaning is performed again.

As described above, according to the drug detection device of the present embodiment, the residual amount of a drug can be computed in a contactless manner by irradiating the target area X with light beams that include near-infrared light and analyzing the reflected light. Also, since the residual amount of a drug can be checked in a short time, the duration for which the production line is stopped can be minimized, and manufacturing efficiency can be improved.

Also, with the above device, the spectrums of the pixels allocated to the entire target area are averaged, and the amount of the drug is computed using average spectral data. Therefore, the volume of data can be reduced and the amount of the drug can be computed quickly.

Second Embodiment

Figure 5:
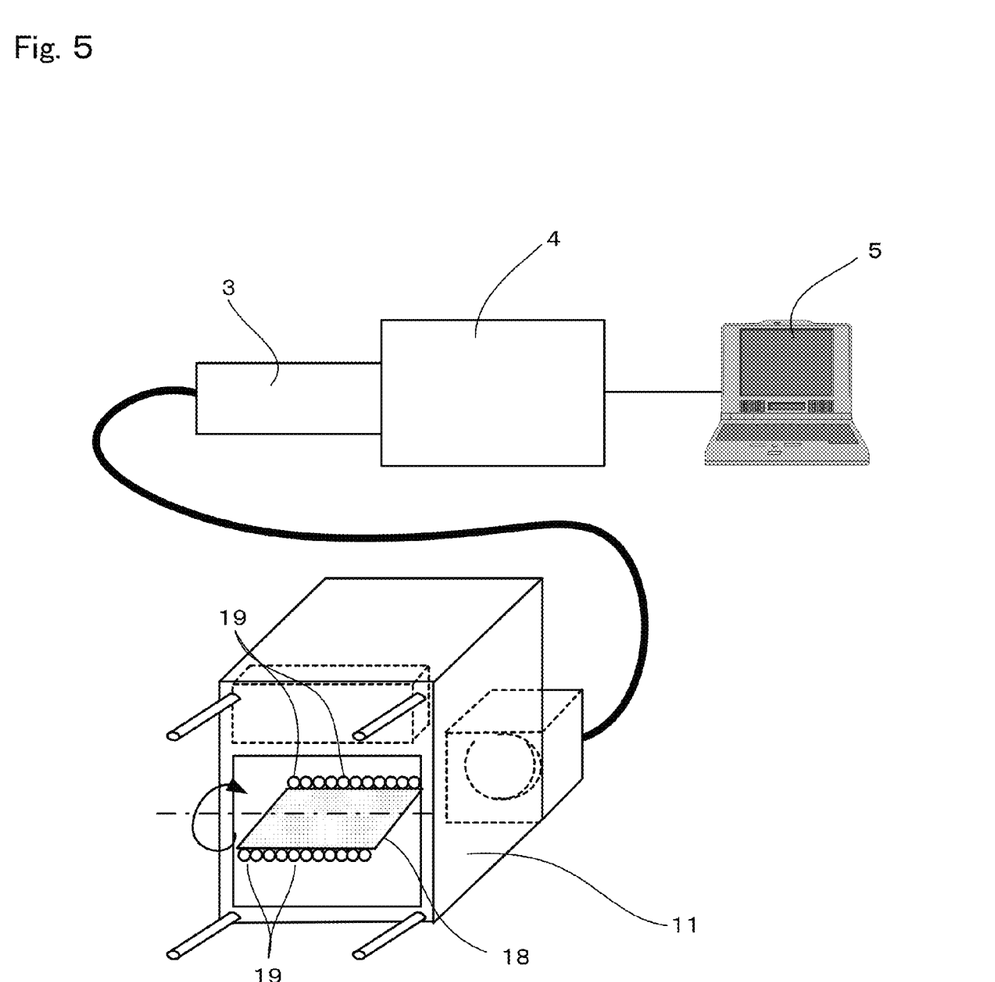
FIG. 5 is a schematic configuration diagram showing a portion of a second embodiment of the drug detection device according to the present invention.

Next, a second embodiment of the drug detection device according to the present invention will be described with reference to FIG. 5. FIG. 5 is a perspective view showing a portion of the drug detection device according to the second embodiment. The present embodiment differs from the first embodiment in the configuration of the light source and the mirror scanner. Hereinafter, the differences from the first embodiment will be described. Note that, in the following embodiments, configuration that is the same as the first embodiment will be given the same reference numerals and description thereof may be omitted.

As shown in FIG. 5, with the device according to the present embodiment, a light source is provided on the periphery of a built-in mirror scanner 18, and a light source is not provided on a supporting member 11. A plurality of light sources 19 that generate little heat can be used as the light source, for example. Also, a gold mirror having a high reflectivity of near-infrared light can be used as the mirror scanner, for example.

Thus, providing the light sources 19 on the periphery of the swingably supported mirror scanner 18 enables imaging to be performed under uniform conditions. Description of the remaining configuration, being the same as the first embodiment, will be omitted.

Third Embodiment

Figure 6:
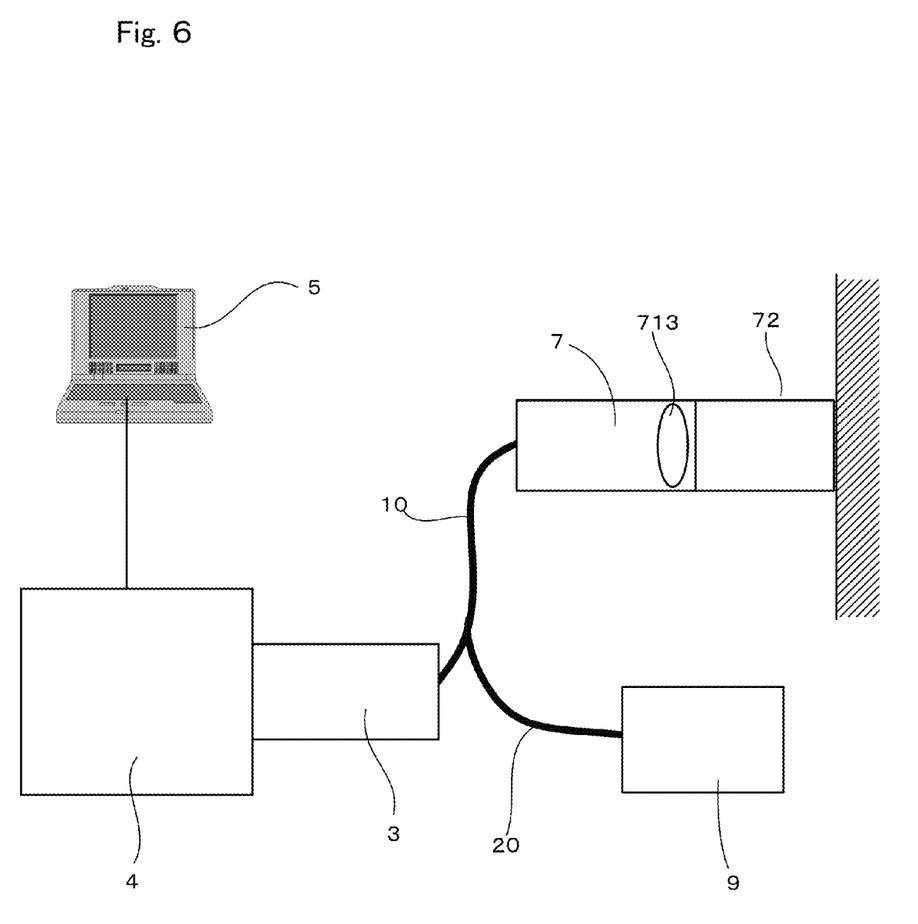
FIG. 6 is a schematic configuration diagram showing a third embodiment of the drug detection device according to the present invention.
Figure 7:
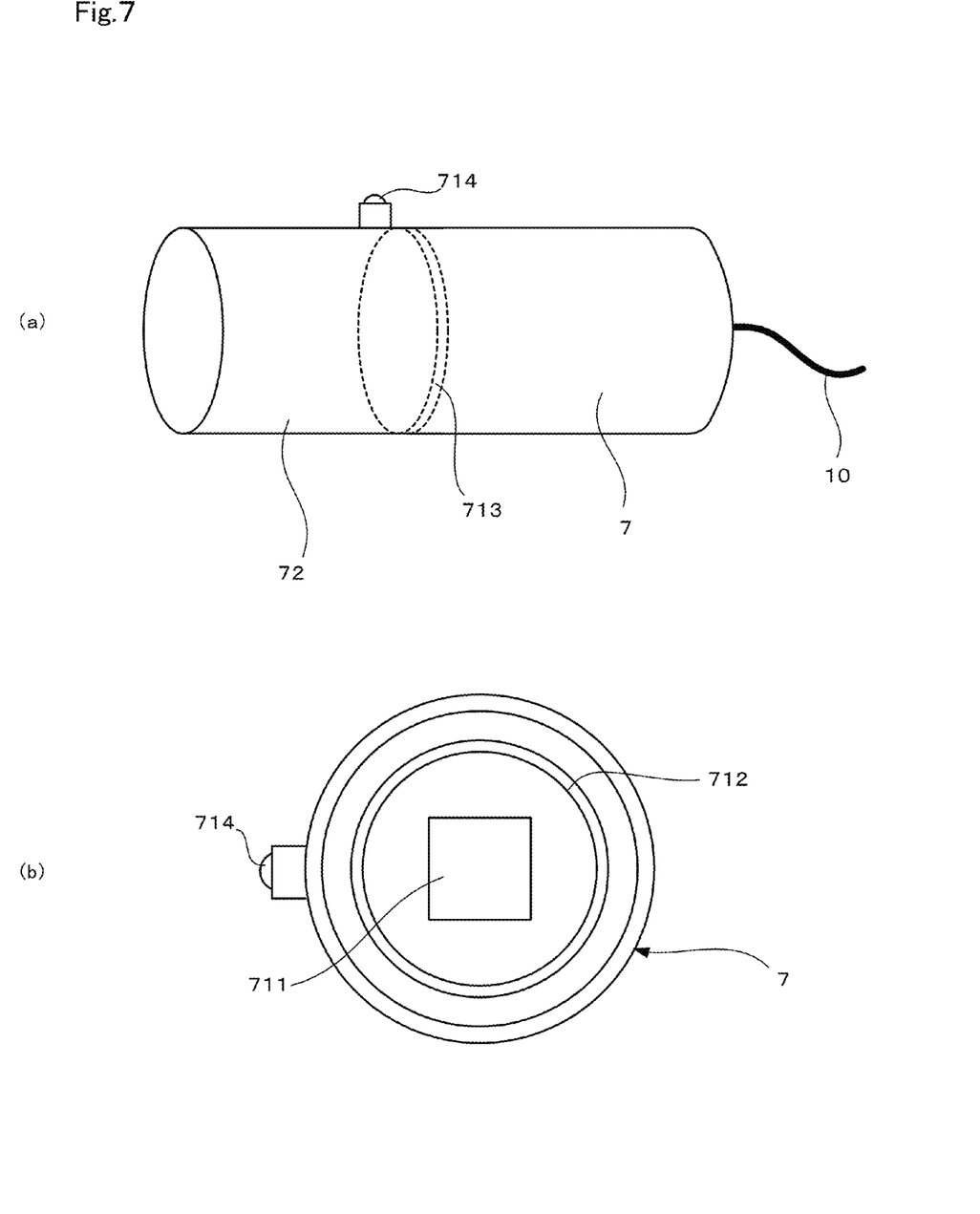
FIG. 7 is (a) a perspective view and (b) a front view of a probe shown in FIG. 6.

Next, a third embodiment of the drug detection device according to the present invention will be described with reference to FIG. 6. FIG. 6 is a schematic configuration diagram showing the drug detection device according to the third embodiment, and FIG. 7 shows a perspective view and a front view of a probe that is used in the present embodiment. The present embodiment differs from the first embodiment in that a supporting member provided with a mirror scanner was used in the first embodiment, whereas a probe is used in the present embodiment. Hereinafter, description will be given focusing on the differences from the first embodiment.

As shown in FIG. 6, with this device, a spectroscope 3 and a probe 7 are connected by an optical fiber cable 10. Also, a light source 9 for supplying a light beam that includes near-infrared light to the probe 7 is provided at a distance from the probe 7. A light supply cable 20 for connecting the light source 9 and the probe 7 is bundled with the optical fiber cable 10. As shown in FIG. 7(a), a lens 713 for image formation and a light receiving unit 711 composed of a plurality of bundled optical fibers are provided inside of the probe 7, and the light receiving unit 711 receives reflected light from the target area through the lens 713. For example, the light receiving surface 711 is constituted by a plurality of optical fibers (e.g., approx. 50 to 100) bundled such that the distal end face is rectangular in shape, as shown in FIG. 7(b). An annular irradiation surface 712 is provided so as to surround this light receiving surface 711. The irradiation surface 712 is constituted so as to enable light from the abovementioned light source 9 to be irradiated toward the target area. Note that the shape of the light receiving surface 711 need not be rectangular, and can be various shapes in accordance with the application, such as circular or polygonal.

Reflected light received by the light receiving surface 711 is transmitted to the spectroscope 3 via the optical fiber cable 10, and an optical spectrum is formed by the spectroscope 3. An image of this optical spectrum is then formed on the imaging surface of the line sensor camera 4 and image data is generated, and the generated image data is sent to the computer 5. At this time, a predetermined number of pixels of the line sensor camera 4 have been allocated to the target area, and the optical spectrums of these pixels are obtained. The subsequent processing will be discussed later.

A cylindrically formed focal point adjustment member 72 is attached at the distal end of the probe 7. This focus point adjustment member 72 is for fixing the distance from the lens 713 to the target area, and a focal point is set in advance based on the distance from the distal end of the focus point adjustment member 72 to the lens 713. Accordingly, the focal point of the lens 713 does not need to be adjusted each time, enabling the target area to be measured quickly. Also, a trigger button 714 is installed on the probe 7, and measurement is started by pressing this trigger button 714 at the measurement point, so that spectral data can be collected.

Next, detection of a drug using the probe 7 having the above configuration will be described. Note that prior to detection of a drug, calibration curves are created, similarly to the first embodiment. First, the target area to undergo inspection is decided. Next, since the measurable area is decided based on the size of the light receiving surface 711 (e.g., 2.5×2.5 $cm^2$), measurement of small areas of this size is repeatedly performed in the case where the measurement area is 10×10 $cm^2$, for example. For example, in the example shown in FIG. 8, 16 small areas Z are set by dividing the target area, and measurement is performed 16 times.

Figure 8:
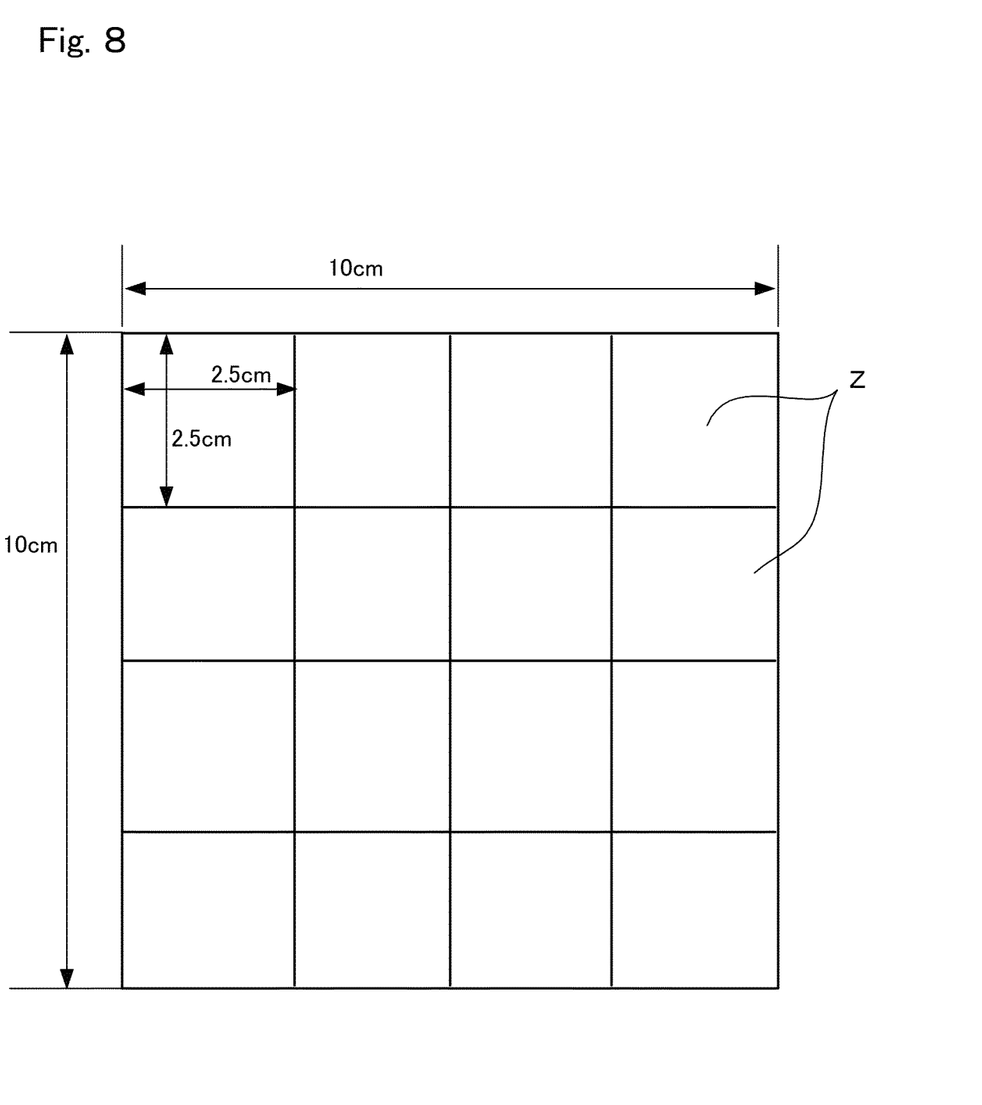
FIG. 8 shows exemplary partitioning of the target area.

In the case of inspecting each small area Z, spectrum collection is performed once in one measurement. When creating a calibration curve, however, spectrum collection is performed a plurality of times similarly to the first embodiment, in order to improve accuracy. While there are various methods of computing the residual amount of a drug, here, for example, an average spectrum is computed from the optical spectrums of the pixels in one small area Z when measurement of that small area is completed, and the residual amount of the drug in the small area Z is computed. The total amount of the drug remaining in the target area can then be computed by adding together the residual amounts of the drug from all the small areas Z.

As described above, according to the present embodiment, the part that performs measurement is constituted by the probe 7, thereby facilitating handling. Also, since a configuration is adopted that enables the light source 9 to be disposed at a distance from the probe 7 and the amount of light from the light source to be supplied via a fiber cable, the measurement operation is facilitated since the area around the measurement point is kept orderly and excessive increases in temperature can also be prevented.

Note that the shape of the probe is not particularly limited, and various configurations can be adopted. For example, the irradiation surface 712 may be rectangular or polygonal in shape, apart from being annular as described above. Also, apart from having a shape that surrounds the light receiving surface 711, the irradiation surface 712 may be adjacent to the light receiving surface 711. Furthermore, rather than incorporating the irradiation surface 712 in the probe head 71, a lighting device having a light source and an irradiation surface can also be attached to the probe head 71.

Although embodiments of the present invention have been described above, the present invention is not limited to these embodiments, and various modifications are possible to the extent that they do not deviate from the gist of the invention. For example, a combination of an area sensor camera and a liquid crystal tunable filter can also be used. An area sensor camera can also be used, apart from a line sensor camera.

The invention claimed is:

1. A drug detection device for detecting a drug remaining in a target area, comprising:
   an irradiation unit configured to irradiate a target area with a light beam that includes near-infrared light;
   a spectroscope on which reflected light from the target area is incident;
   a near-infrared imaging unit configured to capture a spectrum obtained through dispersion of the reflected light by the spectroscope and to generate image data;
   a control unit configured to process the image data; and a storage unit configured to store an equation expressing a relationship between a prescribed amount of a drug and spectral data that is based on the spectrum;

wherein the near-infrared imaging unit is configured to capture each spectrum of a predetermined number of pixels allocated within the target area, and the control unit is configured to compute average spectral data of the area by averaging the spectrums of the pixels, and to compute an amount of the drug corresponding to the average spectral data, based on the equation stored in the storage unit.

2. The drug detection device according to claim 1, further comprising:

a probe in which a light receiving unit configured to receive the reflected light is incorporated, wherein the reflected light is incident on the spectroscope via the light receiving unit.

3. The drug detection device according to claim 2, wherein an irradiation surface from which the irradiation unit emits the light beam is incorporated in the probe.

4. The drug detection device according to claim 3, wherein the irradiation surface is configured so as to surround a light receiving surface on which the light receiving unit receives the reflected light.

5. The drug detection device according to claim 1, wherein the near-infrared imaging unit is a line sensor camera.

6. The drug detection device according to claim 1, wherein the near-infrared imaging unit is a line sensor camera, the device further comprises a minor scanner configured to scan the target area, and reflected light from the target area is caused to be incident on the spectroscope via the minor scanner by scanning the target area in one direction with the minor scanner.

7. The drug detection device according to claim 6, further comprising:

a supporting member configured to support the mirror scanner and to oppose the target area, wherein an opposing surface where the supporting member opposes the target area is black in color.

8. A drug detection method for detecting a drug remaining in a target area, comprising the steps of:

irradiating a target area with a light beam that includes near-infrared light;

causing reflected light from the target area to be incident on a spectroscope;

capturing, with a near-infrared imaging device, a spectrum obtained through dispersion of the reflected light by the spectroscope, and generating image data;

processing the image data; and storing an equation expressing a relationship between a prescribed amount of a drug and spectral data that is based on the spectrum;

wherein the near-infrared imaging device is configured to capture each spectrum of a predetermined number of pixels allocated within the target area, and in the step of processing the image data, average spectral data of the area is computed by averaging the spectrums included in the image data, and an amount of the drug corresponding to the average spectral data is computed based on the equation.

* * * * *